United States Patent [19]

Scholley

[11] Patent Number: 5,036,845

[45] **Date of Patent: * Aug. 6, 1991**

[54] FLEXIBLE CONTAINER FOR COMPRESSED GASES

[76] Inventor: Frank G. Scholley, 922 E. Sparrow Rd., Virginia Beach, Va. 23464

[ * ] Notice: The portion of the term of this patent subsequent to Jun. 12, 2007 has been disclaimed.

[21] Appl. No.: 507,484

[22] Filed: Apr. 11, 1990

Related U.S. Application Data

[63] Continuation of Ser. No. 337,901, Apr. 14, 1989, Pat. No. 4,932,403.

[51] Int. Cl.[5] .......................... A61M 16/08; A62B 7/02; A62B 7/04; A62B 7/10

[52] U.S. Cl. .............................. 128/205.22; 128/204.18

[58] Field of Search ...................... 128/200.24, 201.26, 128/201.27, 201.28, 201.29, 204.18, 205.13, 205.21, 205.22, 201.23, 202.26

[56] References Cited

U.S. PATENT DOCUMENTS

| | | | |
|---|---|---|---|
| 771,801 | 10/1904 | Andrew | 128/201.23 |
| 1,288,857 | 12/1918 | Farr | 128/205.22 |
| 2,380,372 | 7/1945 | Alderfer | 128/205.22 |
| 3,163,707 | 12/1964 | Darling | 128/204.18 |
| 3,338,238 | 8/1967 | Warncke | 128/205.12 |
| 3,491,752 | 1/1970 | Cowley | 128/205.22 |
| 4,253,454 | 3/1981 | Warncke | 128/202.26 |
| 4,932,403 | 6/1990 | Scholley | 128/205.22 |

FOREIGN PATENT DOCUMENTS

| | | | |
|---|---|---|---|
| 971689 | 3/1959 | Fed. Rep. of Germany | 128/205.22 |
| 2644806 | 4/1978 | Fed. Rep. of Germany | 128/205.22 |

*Primary Examiner*—David A. Wiecking

*Assistant Examiner*—Kimberly L. Asher

[57] ABSTRACT

A container is formed of a flexible length of hose, at least a substantial portion of which is of one continuous piece, having alternating expanded-diameter and narrow-diameter storage and connection sections, respectively. The hose includes a liner, a flexible fiber covering the liner, and a flexible protective covering over the fiber. The hose has a pressure gauge at one end and a pressure valve, demand flow regulator and mouthpiece at the other end.

21 Claims, 1 Drawing Sheet

FIG. 1
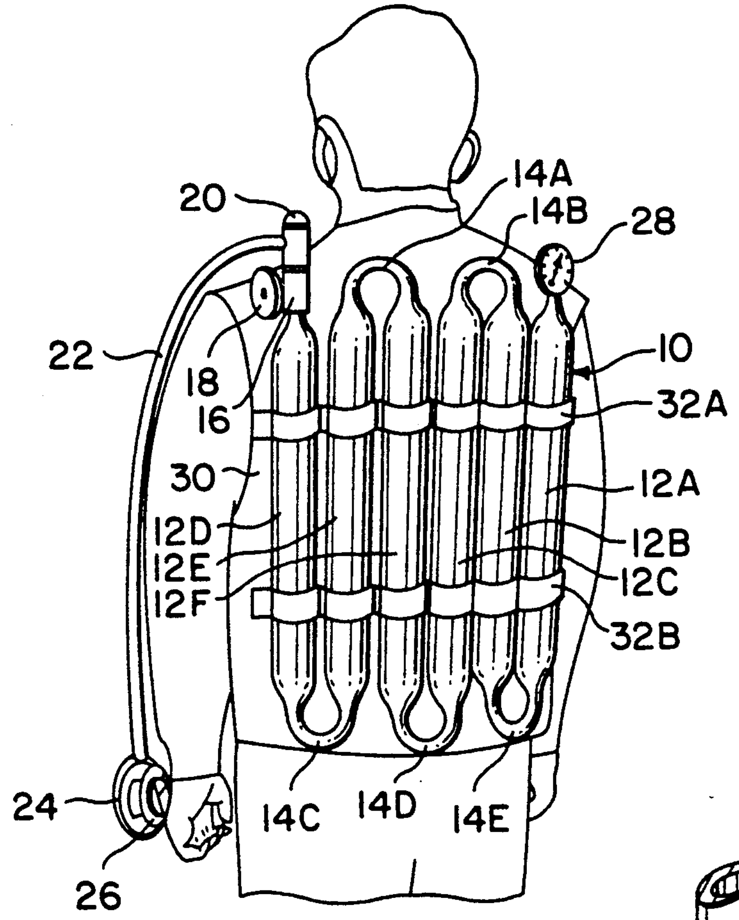
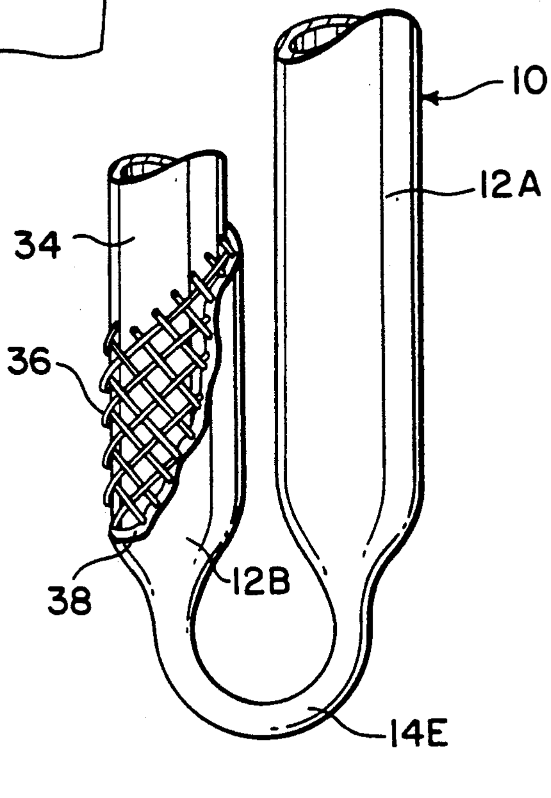
FIG. 2

FLEXIBLE CONTAINER FOR COMPRESSED GASES

CROSS REFERENCE

This is a continuation in part of Application Ser. No. 07/337,901, filed Apr. 14, 1989 and issued as U.S. Pat. No. 4,932,403 on June 12, 1990.

BACKGROUND OF THE INVENTION

1. Field of the Invention

This invention relates to containers for compressed gases, and more particularly for containers which may be carried on a person.

2. Related Art

Divers, fire fighters, miners and alike must perform numerous tasks which require that they carry a portable supply of compressed gases. These gases are usually for breathing in unbreathable environments; however, other gases such as carbon dioxide which are used for extinguishing fires are also carried.

Conventional containers for this purpose are normally of a cylindrical shape with domed ends, and construction is usually of steel or aluminum, or glass fiber wound aluminum. Unfortunately, these containers are cumbersome to wear due to their bulky shape, their ridged structure and their relatively heavy weight. As a result, wearers have difficulty moving in confined spaces, are uncomfortable and are subject to increased levels of fatigue.

Prior approaches such as seen in U.S. Pat. No. 3,338,238 involves a complex, multicell container which can be made in a relatively flat, oval-shape cross section. However, these containers are difficult to manufacture and do not conform to the shape of the wearer.

U.S. Pat. No. 3,491,752 illustrates a slightly flexible pressure vessel made in the form of a coiled spiral tube. This vessel is compact and light weight, but ineffective if more than several minutes of breathing gases are required. While the storage capacity of such a pressure vessel could be increased by using either larger diameter tube or thicker walled tube, the changes are impractical since tubing of increased dimension would not easily coil into a compact shape. U.S. Pat. No. 3,432,060, to the same inventor has similar deficiencies.

U.S. Pat. No. 1,288,857 illustrates a life preserver with a plurality of closed cylinders constructed of rubber, rubber cloth or other suitable air tight fabric, the cylinders being connected together by smaller tubes which are preferably integral with the cylinders. However, the shape, size, and requirement for connecting pipe sections make the unit expensive to manufacture. Further, because of the need for connecting tubes, etc., it cannot be as compact as desirable for personal use.

U.S. Pat. No. 2,380,372 illustrates a flexible, portable container designed to be built into the seat of a parachute that is part of a parachute pack in order to provide oxygen to parachutists. The container includes a length of pipe made in the form of a flat coil, the outer turns of which conform generally to the shape of the seat. The coil of pipe is in the form of a coil in ever decreasing rectangles, squares, or circles which are concentric.

U.S. Pat. No. 1,608,267 is patent which has a life-ring worn around the waist of a user and has a supply of air therein.

German Patent No. 971,689, issued in 1959, includes a plurality of parallel metal cylinders, connected to succeeding cylinders by means of small metal tubes. This particular device is obviously expensive to make and very heavy to wear.

It will be appreciated that the prior types of portable containers had the following disadvantages:

1. If the containers hold more than a few minutes worth of breathing gases, they are large in size and protrude a great distance from the wearer's body. This makes movement through the water or small spaces extremely difficult.

2. Containers designed to hold high pressures are not normally highly flexible. Nonflexible containers do not contour to the wearer's body and are uncomfortable to wear.

3. Containers in use at the present time are normally relatively heavy.

4. The manufacture of existing containers is complex and costly.

OBJECTS AND SUMMARY OF THE INVENTION

One object of the instant invention is to provide a portable container for compressed gases which will protrude only a small distance from the wearer's body.

Another object is to provide a container which is highly flexible and contours to the wearer's body.

A further object is to provide a container which is relatively light weight.

Still another object of the invention is to provide a container which is easily manufactured and is economical.

A further object of the invention is to provide a container which is minimumally protruding, highly flexible, light weight and easy to manufacture, thus providing a portable storage of relatively large volume of compressed gases. This will further enable the wearer to work in small spaces in reasonable comfort and without undue fatigue.

A container is formed of a flexible length of hose, at least a substantial portion of which is of one continuous piece, having alternating expanded-diameter and narrow-diameter storage and connection sections, respectively. The hose includes a liner, a flexible high strength fiber covering the liner and a flexible protective covering over the fiber. The hose can have a pressure gauge at one end and a pressure valve, a demand flow regulator and a mouthpiece at the other end.

BRIEF DESCRIPTION OF THE DRAWINGS

The above and other objects and advantages of the invention will become apparent from the following description and accompanying drawings wherein:

FIG. 1 is a perspective view of a typical embodiment of the container for breathing gases; and FIG. 2 is an enlarged perspective view, in partial cut-away the typical cross section of the container.

DETAILED DESCRIPTION OF THE PREFERRED EMBODIMENT

The preferred embodiment of the present invention is illustrated in FIGS. 1 and 2. The container is made in the form of a one piece, continuous length of hose 10 with expanded-diameter, parallel storage sections 12A–F. The expanded diameter storage sections are connected by alternating narrow-diameter connecting sections 14A–E. The connecting sections are more flexible than the expanded-diameter sections. The arrangement of the expanded-diameter sections in parallel arrangement results in the connecting sections being maintained in a bent attitude as seen in the drawings.

While the preferred embodiment illustrates the expanded-diameter and narrow-diameter sections of all one continuous length, it may be possible for manufacturing considerations to have the hose in more than one section. However, a substantial number of expanded and narrow-diameter sections will be of one continuous length. Also, while the preferred embodiment illustrates the expanded-diameter sections substantially parallel to each other, it is possible that other configurations could be contemplated wherein the expanded-diameter sections form increasingly narrow "concentric" squares or rectangles.

It will be appreciated that the expanded diameter storage sections 12A–F serve as the primary storage spaces for the compressed gases. A typical cross-section of the expanded-diameter storage sections 12A–F is 5 cm in outside diameter. The narrow-diameter connecting sections 14A–E, as stated above, are more flexible than the expanded-diameter sections. The extremely flexible nature of the connecting sections enables the hose 10 to be configured in the disclosed serpentine shape. A typical dimension for the connecting sections 14A--E is 1.5 cm in outside diameter.

Attached to one end of the hose 10 is a valve 16 operated by a handle 18. A known type of pressure regulator 20 is attached to the valve 16, the pressure regulator reducing the pressure of gases which flow into a low pressure tube 22. The tube 22 provides low pressure gases to a known demand flow regulator 24 which is fitted with an inhalation means such as mouthpiece 26. A face piece or mask could also be used. A known pressure indicator 28 is optionally preferably attached to the other end of the hose 10.

The hose 10 is fastened to a vest 30 having arm openings and having an upper strap 32A and a lower strap 32B. In place of the vest, it would be possible to mount the container onto a removable pack and harness arrangement such as used by scuba divers, parachutists and like.

Referring to FIG. 2, a typical cross-section in partial cut-away, of the hose 10 is illustrated. A continuous length of flexible liner 34 is formed of a noncontaminating material such as flexible grade nylon. Other materials such as polyethylene, silicon, vinyl, rubber, polypropylene, polyurethane, tetrafluoroethylene or soft metal can also be used as the liner. The liner could also be constructed of two or more of the previously listed materials. Additionally, the liner could be formed from the same material that is used to impregnate and coat the reinforcing fibers or strands discussed below. In order to provide the container with high pressure capabilities, the liner 34 is seen covered with a high strength reinforcing fiber such as a high strength braid or winding 36. KEVLAR brand aramid fiber made by E. I. Dupont de Nemours is one type of reinforcing fiber that has been found to work well. Other types of fiber material could be thin metal wire, glass, polyester, carbon fiber, graphite or other fibers or hydrids used in composite structures. The fiber can be braided or wound around the liner using a filament winding process. A hybrid braiding and filament winding process could also be used.

In order to prevent abrasion and wear, the fiber braid or winding 36 is preferably coated with a flexible protective covering material such as polyurethane. As seen in FIG. 2, the coating not only covers the fiber 36, but it impregnates and fills the interstices in the braid or winding. Other types of coating material could be silicon, rubber, vinyl, or combinations thereof. More rigid materials such as epoxy, vinylester or polyester resins could also be used. Depending upon the shape and the configuration of expanded and narrow-diameter sections and the intended use, it would be possible to coat the entire group of storage and connecting sections by dipping the configured sections in one simultaneous operation and the shape of the adjacent sections would not be discernable. The container could also be left uncoated if placed inside a protective pouch or shell.

The container illustrated, having six storage sections of 4 cm inside diameter and 60 cm in length, provides a gas storage capacity of approximately 2,700 liters at 600 kg square cm of pressure. This would provide the wearer with about 2 hours of breathing gases where the wearer is working under normal atmospheric conditions. Such a container would weigh approximately 4 kg.

While specific embodiments of the invention have been described and illustrated, it will be clear that variations in the details of the embodiments specifically illustrated and described may be made without departing from the true spirit and scope of the invention as defined in the appended claims.

What is claimed is:

1. A container for compressed gases, comprising:
- a) a length of hose including a liner;
- b) at least a substantial portion of the hose being of one piece and continuous and including alternating expanded-diameter and narrow-diameter sections;
- c) the expanded-diameter sections having a cross-section substantially greater than the cross-sections of the narrow-diameter sections, at least the narrow-diameter sections being flexible;
- d) means for reinforcing and protecting the length of the hose;
- e) the reinforcing and protective means including a flexible fiber of a material selected from the group consisting of aramid fiber, metal wire, fiberglass, carbon fiber and graphite.

2. The flexible container of claim 1, wherein the fiber is a braid.

3. The flexible container of claim 2, wherein a protective covering coats the braid and impregnates the interstices of the braid.

4. The flexible container of claim 1, wherein the fiber is a winding.

5. The flexible container of claim 4, wherein interstices of the winding are impregnated by the protective covering.

6. The flexible container of claim 1, wherein the reinforcing and protective means includes a flexible protective covering.

7. The flexible container of claim 6, wherein the flexible protective covering is of a material selected from the group consisting of polyurethane, silicon, rubber, vinyl, vinylester, epoxy and polyester resins.

8. The flexible container of claim 6, wherein the covering simultaneously covers both expanded-diameter and narrow-diameter sections.

9. The flexible container of claim 6, wherein the covering coats the fiber and impregnates the interstices of the fiber.

10. The flexible container of claim 1, wherein the liner is of a material selected from the group consisting of nylon, polyethylene, silicon, vinyl, rubber, tetrafluorothylene, polypropylene, polyurethane and soft metal.

11. The flexible container of claim 1, wherein the expanded-diameter sections are substantially parallel to each other.

12. The flexible container of claim 1, wherein the narrow-diameter sections are maintained in a bent attitude.

13. The flexible container of claim 1, including a pressure gage connected to the hose.

14. The flexible container of claim 1, wherein the container is mounted on a carrier.

15. The flexible container of claim 14, wherein the carrier is a vest.

16. The flexible container of claim 14, wherein the carrier includes a harness.

17. The flexible container of claim 14, wherein the carrier is worn on a person and extends over the chest and back of the person, and the hose includes a substantial portion on both the front and back of the person.

18. The container of claim 1 wherein the liner is metal.

19. The container of claim 1 wherein the expanded diameter sections are flexible.

20. The flexible container of claim 19, wherein the narrow-diameter sections are more flexible than the expanded-diameter sections.

21. The container of claim 1 wherein the liner is of plastic material.

* * * * *